US00PP23146P2

(12) United States Plant Patent
Danziger

(10) Patent No.: US PP23,146 P2
(45) Date of Patent: Oct. 23, 2012

(54) ***SUTERA* PLANT NAMED 'DANCOP41'**

(50) Latin Name: *Sutera cordata*
Varietal Denomination: DANCOP41

(75) Inventor: Gavriel Danziger, Moshav Mishmar Hashiva (IL)

(73) Assignee: Danziger 'DAN' Flower Form

( * ) Notice: Subject to any disclaimer, the term of this patent is extended or adjusted under 35 U.S.C. 154(b) by 0 days.

(21) Appl. No.: 13/068,512

(22) Filed: May 13, 2011

(51) Int. Cl.
*A01H 5/00* (2006.01)

(52) U.S. Cl. ..... Plt./485

(58) Field of Classification Search ..... Plt./485
See application file for complete search history.

*Primary Examiner* — Annette Para
(74) *Attorney, Agent, or Firm* — Cassandra Bright

(57) ABSTRACT

A new and distinct *Sutera* cultivar named 'DANCOP41' is disclosed, characterized by large, semi-double flowers, early and abundant flowering. The new variety has a compact growth habit and high vigor. The new variety is a *Sutera*, normally produced as an outdoor garden or container plant.

2 Drawing Sheets

Figure 1:
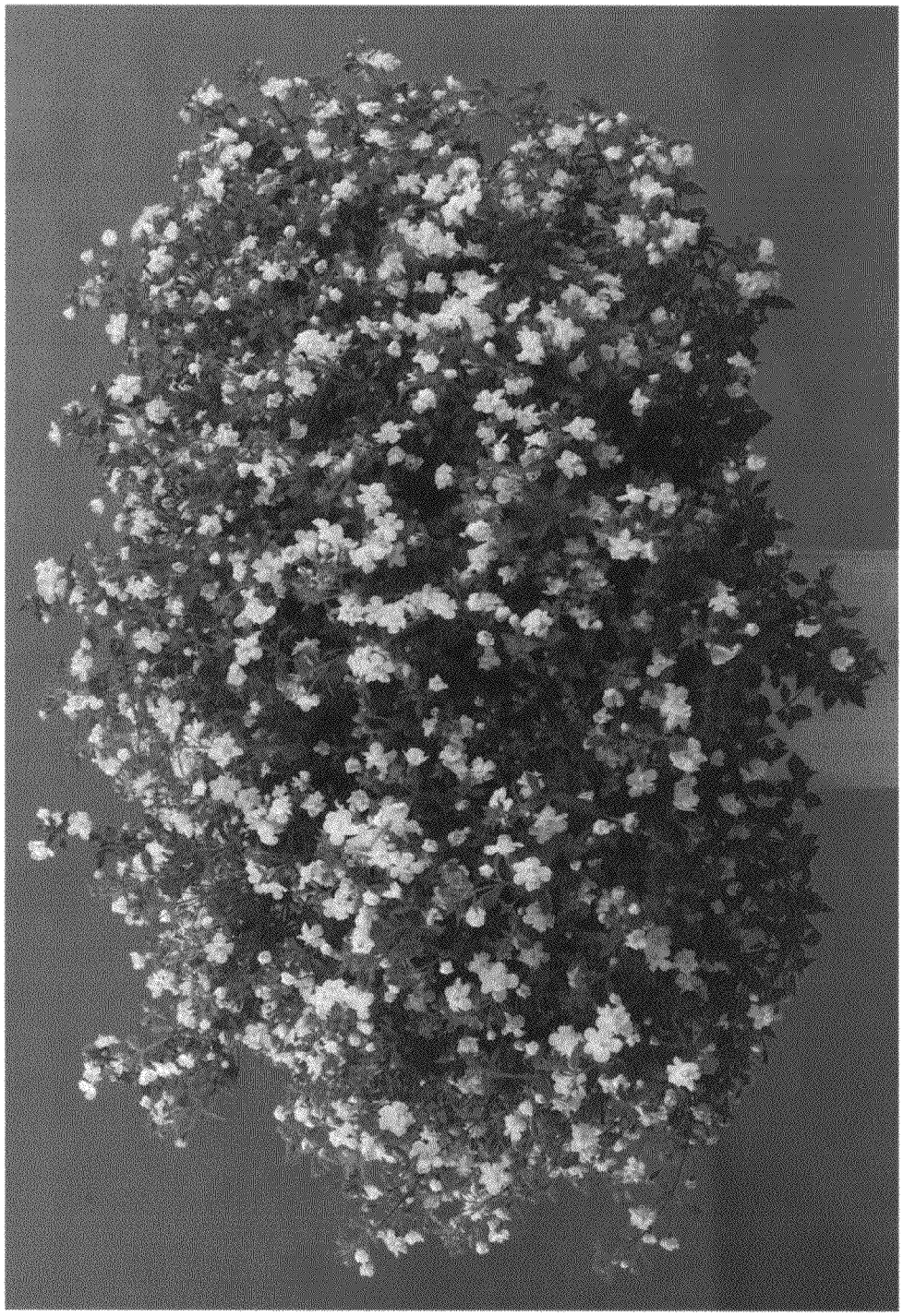

Latin name of the genus and species: *Sutera cordata.*
Variety denomination: 'DANCOP41'.

BACKGROUND OF THE INVENTION

The new *Sutera* cultivar is a product of a planned breeding program conducted by the inventor, Gavriel Danziger, in Moshav Mishmar Hashiva, Israel. The objective of the breeding program was to produce new *Sutera* varieties for ornamental commercial applications. The cross resulting in this new variety was made during February 2008.

The seed parent is the unpatented, proprietary seedling variety referred to as *Sutera cordata* 'Cv-649' The pollen parent is unknown, as the crossing resulting in 'DANCOP41' was an open pollination, with unidentifiable pollen parents. The new variety was discovered in November 2008 by the inventor in a group of seedlings resulting from the February 2008 crossing, in a research greenhouse in Moshav Mishmar Hashiva, Israel.

Asexual reproduction of the new cultivar 'DANCOP41' by vegetative cuttings was first performed at a research greenhouse in Moshav Mishmar Hashiva, Israel in December 2008 and has shown that the unique features of this cultivar are stable and reproduced true to type in successive generations.

SUMMARY OF THE INVENTION

The cultivar 'DANCOP41' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANCOP41' These characteristics in combination distinguish 'DANCOP41' as a new and distinct *Sutera* cultivar:

1. Mounded, compact growth habit
2. Large, semi double white flowers
3. Very free branching plants
4. Early, abundant flowering
5. Vigorous growth Plants of the new cultivar 'DANCOP41' are similar to plants of the seed parent, *Sutera cordata* 'Cv-649' in most horticultural characteristics, however, plants of the new cultivar 'DANCOP41' have a less trailing, more compact plant habit, larger flowers and more branches per plant. Additionally, the new cultivar begins flowering earlier, produces more flowers, and more vigorous plants than the seed parent.

COMMERCIAL COMPARISON

Plants of the new cultivar 'DANCOP41' are comparable to the commercial variety *Sutera* 'SUMSUT03' U.S. Plant Pat. No. 19,085. These *Sutera* varieties are similar in most horticultural characteristics, including flower color and form. The new variety 'DANCOP41' differs in having larger semi-double flowers, somewhat more vigorous growth and an overall more compact plant habit. Additionally, the new variety produces more branches per plant and flowers earlier than 'SUMSUT03'.

Plants of the new cultivar 'DANCOP41' can also be compared to the commercial variety *Sutera* 'Copa Double Blue', unpatented. These varieties are similar in most horticultural characteristics, however 'DANCOP41' has larger flowers of a different color. Additionally, plants of 'DANCOP41' have somewhat more vigorous growth and an overall more compact plant habit. Additionally, the new variety produces more branches per plant and flowers earlier than 'Copa Double Blue'.

BRIEF DESCRIPTION OF THE PHOTOGRAPHS

The accompanying photograph in FIG. 1 illustrates in full color a typical plant of 'DANCOP41' grown in a greenhouse, in a 13 cm basket. Age of the plant photographed is approximately 3 months from a rooted cutting.

Figure 2:
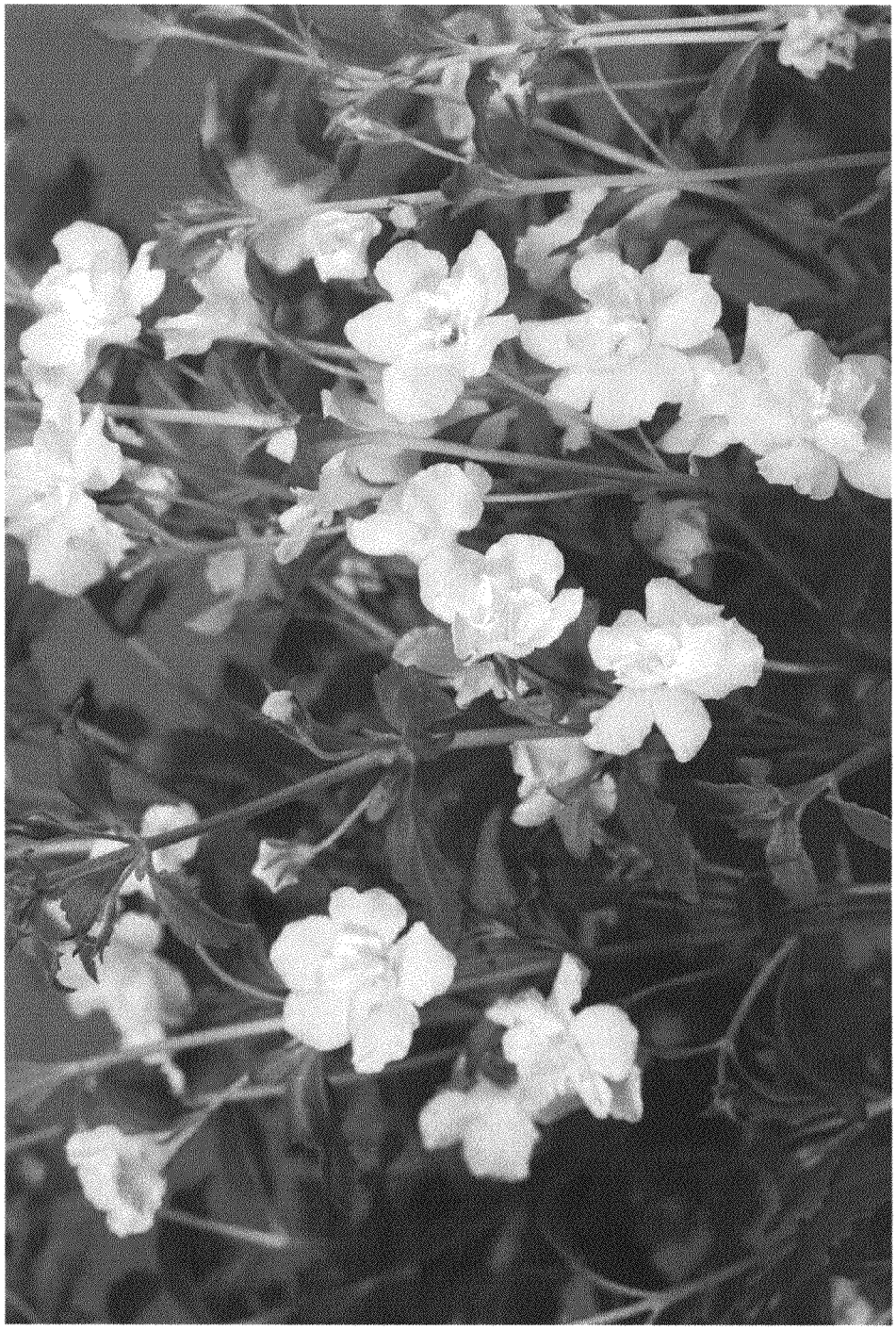

FIG. 2 illustrates in full color a close up of a typical bloom of 'DANCOP41'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DANCOP41' plants grown in a greenhouse during Winter and Spring in Moshav Mishmar Hashiva, Israel. The growing temperature ranged from 15° C. to 26° C. during the day and from 13° C. to 16° C. during the night. General light conditions are bright, normal sunlight. Measurements and numerical values represent averages of typical plant types.
Botanical classification: *Sutera cordata* 'DANCOP41'.

PROPAGATION

Time to initiate roots: About 7 to 10 days at approximately 20° C.
Root description: Fine, fibrous.

PLANT

Growth habit: Semi-trailing, compact.
Pot size of plant described: 13 cm.
Height: Approximately 20 cm.
Plant spread: Approximately 55 cm.
Growth rate: Vigorous.
Branching characteristics: Very free branching.
Length of primary lateral branches: Approximately 35 cm.
Diameter of lateral branches: Approximately 0.2 cm.
Quantity of primary lateral branches: Approximately 10.
Characteristics of primary lateral branches:
- *Form*.—Cylindrical.
- *Diameter*.—Approximately 0.2 cm.
- *Color*.—Near RHS Yellow-Green 146B.
- *Texture*.—Velvety.
- *Strength*.—Strong.

Internode length: Approximately 2.5 cm.

FOLIAGE

Leaf:
- *Arrangement*.—Opposite, petiolate.
- *Quantity*.—Approximately 40 per branch.
- *Average length*.—3.5 cm.
- *Average width*.—2.0 cm.
- *Shape of blade*.—Elliptic.
- *Apex*.—Acute.
- *Base*.—Acuminate.
- *Margin*.—Serrate.
- *Texture of top surface*.—Velvety.
- *Pubescence*.—Slightly pubescent.
- *Aspect*.—Flat.
- *Attachment*.—Approximately 90° angle to branch.
- *Color*.—Young foliage upper side: RHS Green 137 B. Young foliage under side: RHS Green 137 C. Mature foliage upper side: RHS Green 137 A. Mature foliage under side: RHS Green 137 C.
- *Venation*.—Type: Pinnate. Venation color upper side: RHS Green 137 A. Venation color under side: RHS Green 137 C.
- *Petiole*.—Length: Approximately 0.3 cm. Diameter: Approximately 0.2 cm. Color: RHS Green 137A.
- *Texture*.—Slightly velvety.

FLOWER

Natural flowering season: All year round.
Days to flowering from rooted cutting: About 45.
Inflorescence and flower type and habit: Axillary, solitary salverform semi double flowers.
Rate of flower opening: 3 to 5 days from bud to fully opened flower.
Flower longevity on plant: About 7 days.
Persistent or self-cleaning: Persistent.
Bud:
- *Shape*.—Spatulate.
- *Length*.—About 1.3 cm.
- *Diameter*.—About 0.5 cm.
- *Color*.—RHS White 155C.

Flower size:
- *Diameter*.—About 2.3 cm.
- *Length*.—About 1.8 cm.
- *Corolla tube diameter*.—About 0.4 cm.

Corolla/petals:
- *Arrangement*.—Symmetric.
- *Lobe length*.—About 0.9 cm.
- *Lobe width*.—About 1.2 cm.
- *Quantity*.—5 outer petals and 3-5 inner petals.
- *Texture*.—Velvety.
- *Lobe apex*.—Rounded.
- *Lobe shape*.—Rounded.
- *Margin*.—Entire.
- *Color*.—When opening: Upper surface: RHS White 155C. Lower surface: RHS White 155C. Fully opened: Upper surface: RHS White 155C. Lower surface: RHS White 155C. Visible Corolla tube color: RHS Yellow-Orange 21 A.

Calyx/sepals:
- *Quantity per flower*.—5.
- *Shape*.—Linear.
- *Length*.—About 0.9 cm.
- *Width*.—About 0.1 cm.
- *Apex*.—Acute.
- *Base*.—Fused.
- *Margin*.—Entire.
- *Texture*.—Slightly velvety.
- *Color*.—Upper Surface: RHS Green 137 B. Lower Surface: RHS Green 137 B.

Peduncle: None.
Pedicel:
- *Length*.—Approximately 1.5 cm.
- *Diameter*.—Approximately 0.1 cm.
- *Color*.—Near RHS Green 143C.
- *Orientation*.—Slanted upward and outward.
- *Pubescence*.—Slightly pubescent.

Fragrance: None.

REPRODUCTIVE ORGANS

Stamens:
- *Number*.—4.
- *Filament length*.—Approximately 0.8 cm.

Anthers:
- *Shape*.—Cylindrical.
- *Length*.—Approximately 0.1 cm.

*Color*.—RHS Yellow 12A.

*Pollen*.—Color: RHS Yellow 12A. Quantity: Moderate.

Pistil:

*Number*.—1.

*Length*.—About 1.4 cm.

*Style*.—Length: about 1.0 cm. Color: RHS Yellow-Green N144D.

*Stigma*.—Shape: Undulate. Color: RHS Yellow-Green 144B. Ovary Color: RHS Yellow-Green 144A.

OTHER CHARACTERISTICS

Seeds and fruits: About 20 elliptic, small (1 mm long) beige colored seeds per one elliptic Brown capsule.

Disease/pest resistance: Neither resistance nor susceptibility to pathogens and pests common to *Sutera* have been observed.

Temperature tolerance: The new variety tolerates temperatures between 5 to 40° C.

What is claimed is:

1. A new and distinct cultivar of *Sutera* plant named 'DANCOP41' as herein illustrated and described.

* * * * *